US011015988B2

(12) United States Patent
Nirkhe

(10) Patent No.: US 11,015,988 B2
(45) Date of Patent: May 25, 2021

(54) THERMALLY SENSITIVE SLEEVE

(71) Applicant: Johnson & Johnson Surgical Vision, Inc., Santa Ana, CA (US)

(72) Inventor: Chetan P. Nirkhe, Aliso Viejo, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 464 days.

(21) Appl. No.: 15/439,784

(22) Filed: Feb. 22, 2017

(65) Prior Publication Data
US 2018/0238745 A1   Aug. 23, 2018

(51) Int. Cl.
*G01K 11/16* (2021.01)
*A61F 9/007* (2006.01)
*A61L 31/14* (2006.01)
*A61B 17/00* (2006.01)
*A61B 90/00* (2016.01)

(52) U.S. Cl.
CPC .............. *G01K 11/16* (2013.01); *A61F 9/007* (2013.01); *A61F 9/00736* (2013.01); *A61L 31/14* (2013.01); *A61B 2017/00084* (2013.01); *A61B 2017/00831* (2013.01); *A61B 2090/0807* (2016.02); *A61F 9/00745* (2013.01)

(58) Field of Classification Search
CPC ..... G01K 11/16; A61F 9/007; A61F 9/00736; A61F 9/00745; A61B 2017/00084; A61B 2017/00831
USPC ....................................................... 116/216
See application file for complete search history.

(56) References Cited

U.S. PATENT DOCUMENTS

| | | | | |
|---|---|---|---|---|
| 3,651,695 | A * | 3/1972 | Brown ................... | G01K 11/16 374/147 |
| 3,877,411 | A * | 4/1975 | MacDonald .......... | F16C 19/525 116/207 |
| 4,028,118 | A * | 6/1977 | Nakasuji ............... | C08K 5/0041 106/31.19 |
| 4,105,583 | A | 8/1978 | Glover et al. | |
| 4,554,565 | A * | 11/1985 | Kito ....................... | B41M 5/284 374/E11.018 |
| 4,933,525 | A * | 6/1990 | St. Phillips ............ | A47J 36/027 116/216 |
| 5,415,203 | A * | 5/1995 | Huang .................... | F16L 9/12 138/103 |

(Continued)

FOREIGN PATENT DOCUMENTS

KR    20160020297 A    2/2016

OTHER PUBLICATIONS

International Search Report and Written Opinion for Application No. PCT/US2018/019057, dated May 17, 2018, 13 pages.

*Primary Examiner* — Nimeshkumar D Patel
*Assistant Examiner* — Tania Courson
(74) *Attorney, Agent, or Firm* — Johnson & Johnson Surgical Vision, Inc.

(57) ABSTRACT

A method for providing a temperature sensitive element surrounding a surgical instrument to provide a visual indication of tip temperature to an operator of the instrument. Change in color of the element is an indication to the operator to be aware of the generated heat and reduce power to the instrument accordingly. When the tip of a surgical instrument heats up to a certain threshold that would cause harm, a reversible thermochromic property of the element may change colors in direct relation to the rise and fall of temperature.

16 Claims, 2 Drawing Sheets

(56) References Cited

U.S. PATENT DOCUMENTS

| | | | |
|---|---|---|---|
| 5,496,342 A | 3/1996 | Urich | |
| 6,005,484 A * | 12/1999 | Ko | G01K 11/12 |
| | | | 116/207 |
| 6,174,309 B1 * | 1/2001 | Wrublewski | A61B 18/1442 |
| | | | 606/45 |
| 6,706,218 B2 * | 3/2004 | Lucht | C08G 61/126 |
| | | | 116/201 |
| 6,786,897 B2 * | 9/2004 | Mc Ie | A61B 17/00 |
| | | | 374/141 |
| 6,929,136 B2 * | 8/2005 | Salazar-Leal | B65D 51/245 |
| | | | 116/207 |
| 8,633,292 B2 | 1/2014 | Hu et al. | |
| 9,526,585 B2 * | 12/2016 | Pruckner | A61C 1/0015 |
| 10,653,399 B2 * | 5/2020 | Pruckner | A61C 19/04 |
| 2002/0167989 A1 * | 11/2002 | Russo | G01K 1/14 |
| | | | 374/141 |
| 2003/0036747 A1 | 2/2003 | Ie et al. | |
| 2003/0216732 A1 * | 11/2003 | Truckai | A61B 18/14 |
| | | | 606/49 |
| 2003/0216733 A1 * | 11/2003 | McClurken | A61B 18/1442 |
| | | | 606/51 |
| 2007/0032139 A1 * | 2/2007 | Chen | H01R 4/72 |
| | | | 439/877 |
| 2008/0077128 A1 | 3/2008 | Woloszko et al. | |
| 2008/0121171 A1 * | 5/2008 | Hulsey | G01K 11/12 |
| | | | 116/216 |
| 2009/0143516 A1 * | 6/2009 | MacDonald | A61B 5/015 |
| | | | 524/236 |
| 2013/0263352 A1 * | 10/2013 | Crockett, Jr. | A41D 13/0015 |
| | | | 2/69 |
| 2014/0188095 A1 * | 7/2014 | Weber | A61B 18/24 |
| | | | 606/15 |
| 2014/0209842 A1 | 7/2014 | Pagba et al. | |
| 2017/0049424 A1 * | 2/2017 | Pruckner | A61B 90/06 |
| 2018/0008334 A1 * | 1/2018 | Germain | A61B 18/042 |

* cited by examiner

THERMALLY SENSITIVE SLEEVE

BACKGROUND

Field of the Invention

The present invention relates generally to providing a temperature sensitive sleeve and, more particularly, is directed to providing, during a phacoemulsification process, an indication to a physician of temperature changes of a phacoemulsification tip by changing the color of the sleeve and/or at least a portion of the tip of the phacoemulsification handpiece.

Description of the Background

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

As may be appreciated, the flow of fluid to and from a patient through a fluid infusion or extraction system, and thus the control of fluids and fluid pressure through the phacoemulsification handpiece, is critical to the procedure performed. Different medically recognized techniques have been utilized to control the fluid flow during the lens removal portion of the surgery. Among these, one popular technique is a simultaneous combination of phacoemulsification, irrigation and aspiration using a single handpiece. This method includes making the incision, inserting the handheld surgical implement to emulsify the cataract or eye lens, and, simultaneously with this emulsification, having the handpiece provide a fluid for irrigation of the emulsified lens using a sleeve that surrounds a needle and a vacuum for aspiration of the emulsified lens and inserted fluids.

Currently available phacoemulsification systems, such as those mentioned above, typically include a variable speed peristaltic pump and/or vacuum pump, a vacuum sensor, an adjustable source of ultrasonic power, and a programmable microprocessor with operator-selected presets for controlling aspiration rate, vacuum and ultrasonic power levels. The phacoemulsification handpiece is interconnected with a control console by an electric cable for powering and controlling a piezoelectric transducer that drives the action of the handpiece. Tubing provides irrigation fluid to the eye through the handpiece and enables withdrawal of aspiration fluid from an eye through the handpiece.

Generally, irrigation and aspiration are employed by the surgeon using the device to remove unwanted tissue and maintain pressure within the eye. Moreover, the use of, and particularly the pressurization of, the irrigation fluid is critical and may, for example, prevent the collapse of the eye during the removal of the emulsified lens. Irrigation fluid pressure is also used to protect the eye from the heat generated by the ultrasonic cutting needle and may suspend fragments created during the surgery in fluid for more easy removal through aspiration.

During a phacoemulsification process, such as a process for cataract removal in an ophthalmic procedure, heat may be generated due to use of ultrasonic energy and cavitation. The heat generated, if not controlled by use of adequate infusion of fluid through a sleeve can result in cornea burn of a patient. Typically, the heat generated during a phacoemulsification procedure is not measured and it is at the discretion of the physician performing the procedure to either reduce or increase phacoemulsification energy and balance fluid inflow as needed to remove a cataract. Without proper temperature regulation, a corneal burn of the patient may occur inadvertently.

In the conventional art, Glover et al. (U.S. Pat. No. 4,105,583) taught a thermochromic paint that changes color when heated to a certain temperature. The thermochromic paint may be used on a plastic surface. Upon heating to a temperature sufficient to cause the loss of the water of hydration from the pigment, the coating changes color, indicating visually that a particular temperature has been reached.

Pagba et al. (U.S. 2014/0209842 A1) taught a silicone-based material that incorporates a photochromic molecule wherein the material changes color when exposed to ultraviolet radiation. After the source of ultraviolet radiation is removed, the material reverts to its original color.

Hu et al. (U.S. Pat. No. 8,633,292) taught a photochromic composition for making optical materials comprising a polyurethane prepolymer formed by combining an isocyanate and a compound having an active hydrogen containing group, a polysilsequioxane and a photochromic compound. Optical materials, such as optical lenses comprising the photochromic composition, may transition between light and dark states based on environment (indoor vs. outdoor).

Thus, there is a need for a system and method that provides a clear visual indication of temperature level of a surgical instrument's tip on the surgical instrument to prevent patient injury.

SUMMARY OF THE INVENTION

The present disclosure is directed to a system for providing a temperature sensitive sleeve to provide a visual indication of surgical instrument tip temperature to an operator of the instrument. Change in color of the sleeve may be an indication to the operator of the heat being produced and to possibly reduce power to the instrument accordingly. When the tip of a surgical instrument heats up to a certain threshold that would cause harm, a reversible thermochromic/thermochromatic element in the sleeve material may change colors in direct relation to the rise in temperature.

Accordingly, the disclosure provides a system and method that provides improved surgical instrument tip temperature regulation to a surgical site.

DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

In an embodiment of the present invention, a handheld surgical implement may be encased at least partially by a temperature sensitive sleeve. In another embodiment of the present invention, a handheld surgical implement may be, for example, a phacoemulsification surgical handheld device which comprises a reversible thermochromic ring and a phacoemulsification tip.

Figure 1:
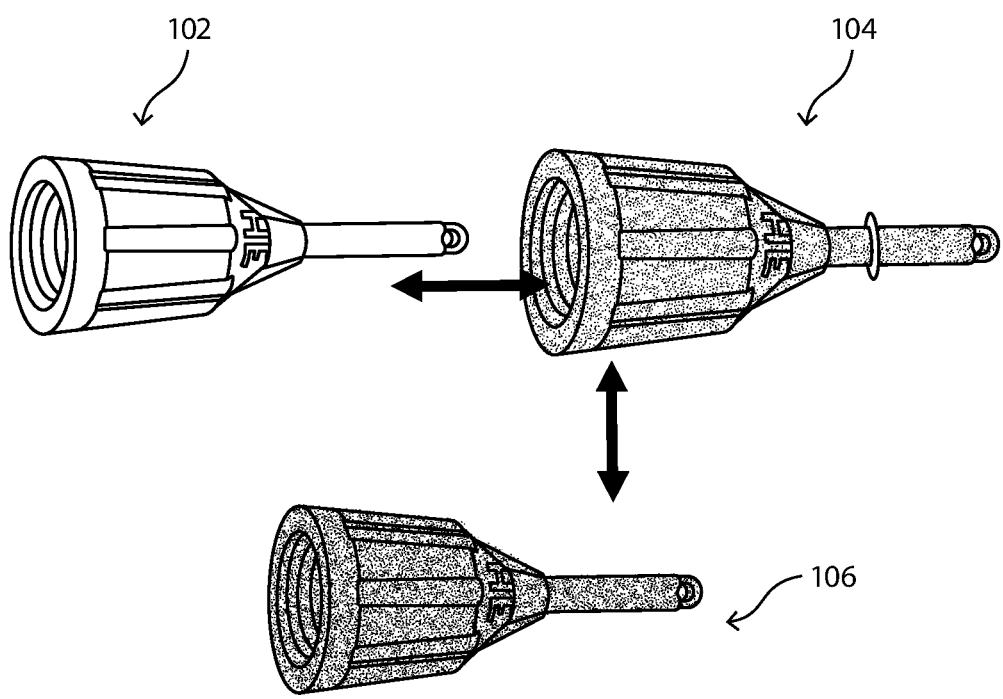
FIG. 1 is a pictorial depiction of color change in a temperature sensitive sleeve.

In an embodiment of the present invention, a surgical implement encased within a temperature sensitive sleeve is illustrated in FIG. 1. The sleeve may be able to change to a specific color depending on the temperature sensitivity desired and thermochromic/thermochromatic additive or component material used for the polymer/soft material sleeve when going from cold to hot and vice versa. For example, as illustrated by FIG. 1, state 102 may indicate low temperature, state 104 may indicate warm temperature, and state 106 may indicate hot temperature (e.g., >37° C.). Arrows of FIG. 1 indicate reversible color change between the states (e.g., 102↔104; 104↔106). Based on color indication, a surgeon, such as an ophthalmic physician, may be made readily aware of the heat generated and will be inclined to reduce power to the surgical element accordingly. The temperature sleeve material may include a reversible thermochromic material additive or component in a polymeric/soft material mix. Reversible thermochromic material additives could be custom designed to operate in the range of 20° C. to 68° C. for extreme cases where multiple color changes are depicted in the material depending on the range of the temperature. The reversible thermochromic additives could be organic or inorganic materials that can be introduced in a polymeric/soft material matrix to form the final compound. The thermochromic additives could be but not limited to liquid crystals or lueco dyes depending on the desired temperature range and formulation. Base polymeric materials could comprise of polyurethane, or polyolefins. Soft rubber like materials to which the reversible thermochromic element that could be added may be comprised of one or more of the following: silicone, thermoplastic elastomer, TPU rubber, or soft grades of Pebax polymer.

Figure 2:
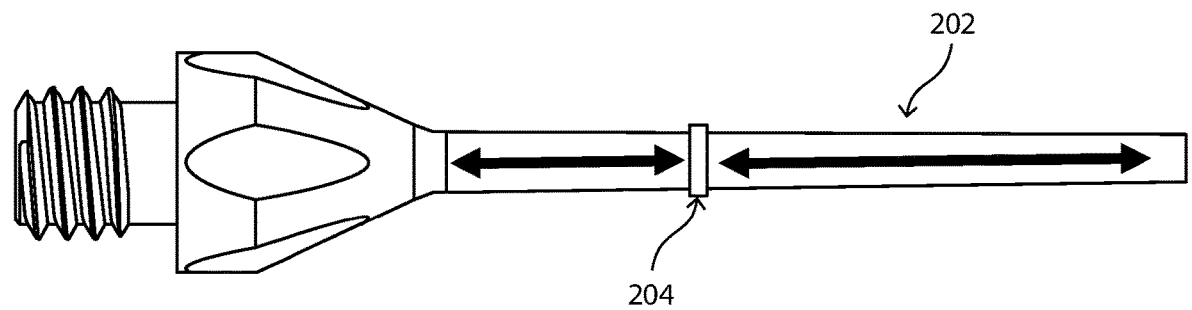
FIG. 2 illustrates an embodiment of the surgical instrument of the present invention.

In an embodiment of the present invention, a surgical implement, such as that illustrated in FIG. 2, may comprise a reversible thermochromic ring 204 assembled around or on top of a phacoemulsification tip 202. The reversible thermochromic ring may be able to change to a specific color depending on the temperature sensitivity desired. For example, the ring may be optimized with at least one reversible thermochromic property that does not respond to normal operating temperatures during a phacoemulsification process and instead indicates high temperatures (e.g., above 37° C.). Based on color indication, a surgeon, such as an ophthalmic physician, may be made readily aware of the heat generated and will be inclined to reduce power to the surgical element accordingly. The reversible thermochromic ring material may include a thermochromic material additive or component in a polymeric/soft material mix. The polymeric material may be one or more of the following: a thermoplastic such as polyurethane, Pebax or polyolefin and/or an elastomeric soft material such as silicone, TPE, TPU rubber, etc.

Figure 3:
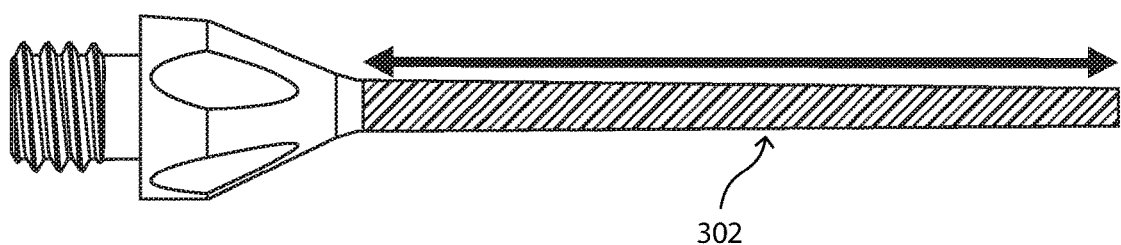
FIG. 3 illustrates a schematic diagram of the surgical instrument of the present invention.

In a further embodiment of the present invention, a surgical element 300, such as that illustrated in FIG. 3, may comprise a reversible thermochromic/thermochromatic paint or ink layer 302 around or on top of a phacoemulsification tip. The paint/ink layer may provide a visual indication of the surgical instrument's tip temperature to an operator of the instrument. A change in color of the phacoemulsification tip may be an indication to the operator of the heat being produced and thereby cause the operator to reduce power to the instrument accordingly. When the phacoemulsification tip heats up to a certain temperature threshold (e.g., above 55° C.) that would cause harm, the reversible thermochromic/thermochromatic paint or ink layer on the surface of the phacoemulsification tip may change colors in direct relation to the rise and fall in temperature.

The reversible thermochromic/thermochromatic paint/ink may, for example, be applied by spray coating, dip coating, or surface modification to the phacoemulsification tip material. The reversible thermochromic/thermochromatic paint/ink may be organic or inorganic in origin with solvent, UV, or a water-based mixture. In practice, some or all of the phacoemulsification tip may exhibit the reversible thermochromic/thermochromatic property.

Those of ordinary skill in the art may recognize that many modifications and variations of the herein disclosed systems and methods may be implemented without departing from the spirit or scope of the invention. Thus, it is intended that the present invention covers such modifications and variations provided they come within the scope of the appended claims and their equivalents.

What is claimed is:

1. A system for providing visual indications of temperature changes in a surgical instrument during an ocular surgery, the system comprising:
   an ocular surgical instrument comprising at least one tip for performing the ocular surgery; and,
   a reversible thermochromic covering on the at least one tip that changes color in response to a temperature change in the at least one tip during the ocular surgery;
   wherein the reversible thermochromic covering has a first color indicating that the at least one tip has a temperature equal to or greater than 37° C. and has a different color indicating that the at least one tip has a temperature below 37° C.

2. The system of claim 1, wherein the surgical instrument is a phacoemulsification handpiece.

3. The system of claim 1, wherein the reversible thermochromic covering comprises one or more polymeric or soft material with at least one reversible thermochromic component.

4. The system of claim 3, wherein the polymeric or soft material is one or more material selected from the group consisting of polyurethane, polyolefin, silicone, and thermoplastic elastomer (TPE).

5. A system for providing visual indications of temperature changes during an ocular surgery, the system comprising:
a surgical instrument having at least one tip configured for performing the ocular surgery; and
a thermochromic ring partially covering a portion of the at least one tip of the surgical element, wherein the thermochromic ring changes color in response to a change in temperature at the at least one tip during the ocular surgery;
wherein the thermochromic ring has a first color when the temperature at the at least one tip is 37° C. and above and has a different color when the temperature at the at least one tip is below 37° C.

6. The system of claim 5, wherein the surgical instrument is a phacoemulsification handpiece.

7. The system of claim 5, wherein the thermochromic ring comprises at least one polymeric or soft material with at least one reversible thermochromic component.

8. The system of claim 7, wherein the polymeric or soft material is one or more material selected from the group consisting of polyurethane, polyolefin, silicone, and thermoplastic elastomer (TPE).

9. A system for providing a visual indication of a temperature change during use of a surgical instrument in an ocular surgery, the system comprising:
an ocular surgical instrument having at least one tip for performing the ocular surgery; and
a reversible thermochromic covering on a portion of the at least one tip that changes color based on a temperature at the at least one tip;
wherein the reversible thermochromic covering has at least three different colors, and wherein one color indicates that the at least one tip has a temperature of at least 37° C. and each of the other two colors indicate that the at least one tip has a temperature of less than 37° C.

10. The system of claim 9, wherein the surgical instrument is a phacoemulsification handpiece.

11. The system of claim 9, wherein the reversible thermochromic covering comprises at least one polymeric or soft material with at least one reversible thermochromic component.

12. The system of claim 11, wherein the polymeric or soft material is one or more material selected from the group consisting of polyurethane, polyolefin, silicone, and thermoplastic elastomer (TPE).

13. The system of claim 9, wherein the reversible thermochromic covering is a sleeve or a ring.

14. The system of claim 9, wherein the reversible thermochromic covering is a paint.

15. A system for providing visual indications of temperature changes during a surgical procedure, the system comprising:
a phacoemulsification handpiece having a tip for performing the surgical procedure; and,
a reversible thermochromic element partially covering the tip,
wherein the reversible thermochromic element is a paint or ink on the tip that changes color based on a temperature of the tip.

16. A instrument for use with a phacoemulsification handpiece in an ocular surgical procedure, the instrument comprising:
a tip for performing the ocular surgical procedure; and,
a reversible thermochromic coating on a portion of the tip that changes color based on a temperature of the tip,
wherein the reversible thermochromic coating has a first color indicating that the tip has a temperature equal to or greater than 37° C. and has a different color indicating that the tip has a temperature below 37° C.

* * * * *